(12) United States Patent
Shakespeare et al.

(10) Patent No.: US 9,109,330 B2
(45) Date of Patent: Aug. 18, 2015

(54) APPARATUS AND METHOD FOR MEASURING PROPERTIES OF UNSTABILIZED MOVING SHEETS

(75) Inventors: John F. Shakespeare, Hiltulanlahti (FI); Tarja T. Shakespeare, Hiltulanlahti (FI); Markku Kellomäki, Kuopio (FI)

(73) Assignee: Honeywell International Inc., Morristown, NJ (US)

(*) Notice: Subject to any disclaimer, the term of this patent is extended or adjusted under 35 U.S.C. 154(b) by 799 days.

(21) Appl. No.: 12/400,661

(22) Filed: Mar. 9, 2009

(65) Prior Publication Data
US 2010/0228518 A1 Sep. 9, 2010

(51) Int. Cl.
G01B 11/04 (2006.01)
G01B 11/06 (2006.01)
G01N 21/86 (2006.01)
D21G 9/00 (2006.01)
G01B 11/02 (2006.01)
(Continued)

(52) U.S. Cl.
CPC ............ D21G 9/0009 (2013.01); G01B 11/026 (2013.01); G01B 11/06 (2013.01); G01N 21/86 (2013.01); G01N 21/89 (2013.01); G01B 11/0691 (2013.01); G06F 17/18 (2013.01)

(58) Field of Classification Search
CPC ...... D21G 9/0009; G01N 21/86; G01N 21/89; B65H 7/02; G01B 11/06; G01B 11/026; G06F 17/18
See application file for complete search history.

(56) References Cited

U.S. PATENT DOCUMENTS

| | | |
|---|---|---|
| 3,103,850 A | 9/1963 | Khoury at al. |
| 3,386,635 A | 6/1968 | Nash |
| 4,052,599 A | 10/1977 | Whiteley et al. |

(Continued)

FOREIGN PATENT DOCUMENTS

| | | |
|---|---|---|
| DE | 102004007374 | 8/2005 |
| EP | 1112951 | 7/2001 |

(Continued)

OTHER PUBLICATIONS

International Search Report and Witten Opinion of the International Searching Authority in PCT Application No. PCT/US2007/086464 dated Apr. 8, 2008.

(Continued)

*Primary Examiner* — Janet Suglo
*Assistant Examiner* — L. Anderson

(57) ABSTRACT

A method includes receiving multiple biased measurements associated with a property of a sheet of material, where the biased measurements correspond to multiple known sheet geometries. The method also includes determining an unbiased measurement associated with the property of the sheet using the biased measurements, where the unbiased measurement corresponds to a nominal sheet geometry. The method further includes storing and/or outputting the unbiased measurement. Determining the unbiased measurement could include performing regression using the biased measurements and their corresponding sheet geometries to identify an estimated value of the property of the sheet at the nominal sheet geometry. The biased measurements can be generated using one or more sensors, and the sheet may not be stabilized during the biased measurement generation. Additional sheet geometries can also be created, such as by varying a tilt angle, a curvature, and/or a position of the sheet.

20 Claims, 3 Drawing Sheets

(51) Int. Cl.
*G01N 21/89* (2006.01)
*G06F 17/18* (2006.01)

(56) References Cited

U.S. PATENT DOCUMENTS

| | | | |
|---|---|---|---|
| 4,672,841 A | 6/1987 | Schuster et al. | |
| 4,748,331 A | 5/1988 | Nagao et al. | |
| 4,877,485 A | 10/1989 | Carson | |
| 4,938,404 A | 7/1990 | Helms et al. | |
| 5,440,238 A | 8/1995 | Martens et al. | |
| 5,488,476 A | 1/1996 | Mansfield et al. | |
| 5,634,636 A * | 6/1997 | Jackson et al. | 271/225 |
| 5,678,447 A | 10/1997 | Graff | |
| 5,793,486 A | 8/1998 | Gordon et al. | |
| 5,900,937 A | 5/1999 | Wang | |
| 5,928,475 A * | 7/1999 | Chase et al. | 162/198 |
| 6,166,393 A | 12/2000 | Paul et al. | |
| 6,281,679 B1 | 8/2001 | King et al. | |
| 6,397,667 B1 | 6/2002 | Fujii et al. | |
| 6,429,944 B1 | 8/2002 | Flormann | |
| 6,542,248 B1 | 4/2003 | Schwarz | |
| 6,734,670 B2 | 5/2004 | Crouzen | |
| 6,743,338 B2 | 6/2004 | Graeffe et al. | |
| 6,936,137 B2 | 8/2005 | Moeller et al. | |
| 6,965,836 B2 | 11/2005 | Richardson | |
| 7,146,279 B2 | 12/2006 | Typpoe et al. | |
| 7,199,884 B2 * | 4/2007 | Jasinski et al. | 356/632 |
| 7,325,445 B1 | 2/2008 | Bowman | |
| 2007/0260335 A1 * | 11/2007 | Fan et al. | 700/29 |
| 2008/0136091 A1 | 6/2008 | Shakespeare | |
| 2009/0184463 A1 | 7/2009 | Shakespeare et al. | |

FOREIGN PATENT DOCUMENTS

| | | |
|---|---|---|
| WO | WO 03/035974 A1 | 5/2003 |
| WO | WO 2004/015197 A1 | 2/2004 |

OTHER PUBLICATIONS

Notification of Transmittal of the International Search Report and the Written Opinion of the International Searching Authority, or the Declaration dated Sep. 29, 2010 in connection with International Patent Application No. PCT/US2010/025988.

Supplementary European Search Report dated Jun. 28, 2012 in connection with European Patent Application No. EP 10 75 1188.

* cited by examiner

APPARATUS AND METHOD FOR MEASURING PROPERTIES OF UNSTABILIZED MOVING SHEETS

TECHNICAL FIELD

This disclosure relates generally to measurement systems and more specifically to an apparatus and method for measuring properties of unstabilized moving sheets.

BACKGROUND

Sheets of material are often used in various industries and in a variety of ways. These materials can include paper, plastic, and other materials manufactured or processed in webs or sheets. As a particular example, long sheets of paper or other materials can be manufactured and collected in reels.

It is often necessary or desirable to measure one or more properties of a sheet of material as the sheet is being manufactured or processed. For example, in a paper sheet-making process, it is often desirable to measure properties of the sheet (such as its color, gloss, or haze) to verify whether the sheet is within certain specifications. Adjustments can then be made to the sheet-making process to ensure the sheet properties are within the desired range(s).

Many optical and image-based measurements involving a sheet often require the sheet to be confined in a specific position or plane. For example, there is often a narrow range of working distances (from a sensor to the sheet) and/or a narrow range of tilt angles (with respect to illumination or examination of the sheet) that provide proper measurements of the sheet. Deviations from the expected or required distances, angles, or other geometries may introduce bias, uncertainty, or other errors in the measurements. This problem becomes more pronounced when taking measurements of a moving sheet, which may flutter or otherwise move as it passes by or between sensors.

Existing solutions for constraining sheet geometries are often of limited use. For example, solutions that stabilize a sheet for one sensor may disturb the sheet near other sensors. As another example, contacting solutions actually touch the sheet, which can apply friction to the sheet. This may create markings on the sheet, increase the risk of a sheet break, and create difficulties in setting up the contacting solutions. As yet another example, aerodynamic devices often do not guarantee good sheet position or sheet planarity since the sheet's position may be unstable in time and can vary with sheet tension.

SUMMARY

This disclosure provides an apparatus and method for measuring properties of unstabilized moving sheets.

In a first embodiment, a method includes receiving multiple biased measurements associated with a property of a sheet of material, where the biased measurements correspond to multiple known sheet geometries. The method also includes determining an unbiased measurement associated with the property of the sheet using the biased measurements, where the unbiased measurement corresponds to a nominal sheet geometry. The method further includes storing and/or outputting the unbiased measurement.

In a second embodiment, an apparatus includes at least one memory configured to store multiple biased measurements associated with a property of a sheet of material, where the biased measurements correspond to multiple known sheet geometries. The apparatus also includes at least one processor configured to determine an unbiased measurement associated with the property of the sheet using the biased measurements, where the unbiased measurement corresponds to a nominal sheet geometry.

In a third embodiment, a computer readable medium embodies a computer program. The computer program includes computer readable program code for obtaining multiple biased measurements associated with a property of a sheet of material, where the biased measurements correspond to multiple known sheet geometries. The computer program also includes computer readable program code for determining an unbiased measurement associated with the property of the sheet using the biased measurements, where the unbiased measurement corresponds to a nominal sheet geometry. The computer program further includes computer readable program code for adjusting operation of a system producing the sheet based on the unbiased measurement.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 6, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
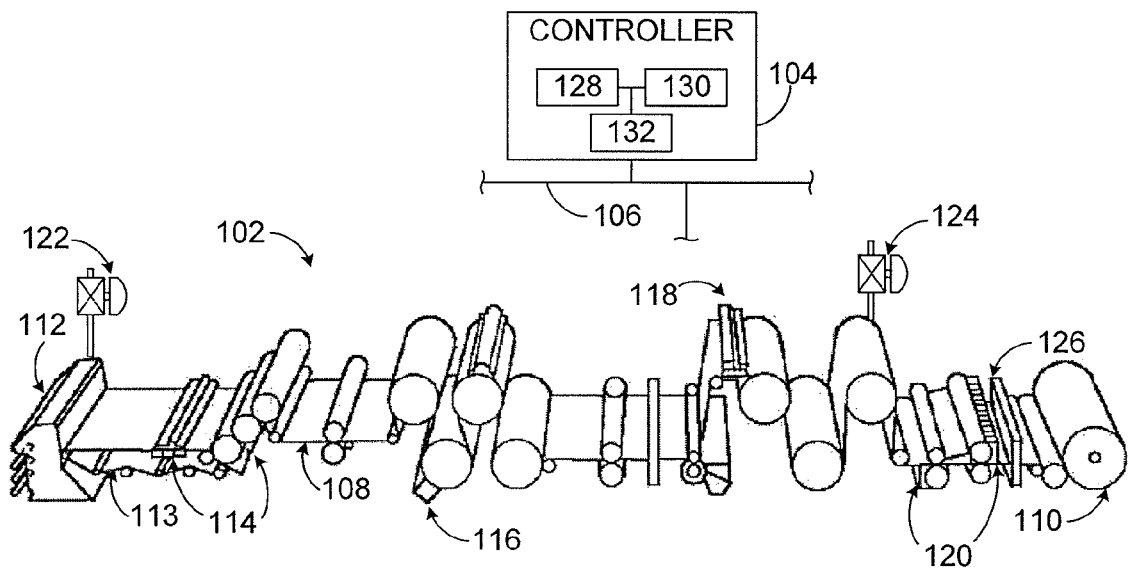
FIG. 1 illustrates an example paper production system according to this disclosure.

FIG. 1 illustrates an example paper production system 100 according to this disclosure. In this example, the paper production system 100 includes a paper machine 102, a controller 104, and a network 106. The paper machine 102 includes various components used to produce a paper product, namely a paper sheet 108 collected at a reel 110. The controller 104 monitors and controls the operation of the paper machine 102, which may help to maintain or increase the quality of the paper sheet 108 produced by the paper machine 102.

In this example, the paper machine 102 includes a headbox 112, which distributes a pulp suspension uniformly across the machine onto a continuous moving wire screen or mesh 113. The pulp suspension entering the headbox 112 may contain, for example, 0.2-3% wood fibers, fillers, and/or other materials, with the remainder of the suspension being water. The headbox 112 may include an array of dilution actuators, which distributes dilution water into the pulp suspension across the sheet. The dilution water may be used to help ensure that the resulting paper sheet 108 has a more uniform basis weight across the sheet 108. The headbox 112 may also include an array of slice lip actuators, which controls a slice opening across the machine from which the pulp suspension exits the headbox 112 onto the moving wire screen or mesh 113. The array of slice lip actuators may also be used to control the basis weight of the paper or the distribution of fiber orientation angles of the paper across the sheet 108.

An array of drainage elements 114, such as vacuum boxes, removes as much water as possible. An array of steam actuators 116 produces hot steam that penetrates the paper sheet 108 and releases the latent heat of the steam into the paper sheet 108, thereby increasing the temperature of the paper sheet 108 in sections across the sheet. The increase in temperature may allow for easier removal of water from the paper sheet 108. An array of rewet shower actuators 118 adds small droplets of water (which may be air atomized) onto the surface of the paper sheet 108. The array of rewet shower actuators 118 may be used to control the moisture profile of the paper sheet 108, reduce or prevent over-drying of the paper sheet 108, or correct any dry streaks in the paper sheet 108.

The paper sheet 108 is then often passed through a calender having several nips of counter-rotating rolls. Arrays of induction heating actuators 120 heat the shell surfaces of various ones of these rolls. As each roll surface locally heats up, the roll diameter is locally expanded and hence increases nip pressure, which in turn locally compresses the paper sheet 108. The arrays of induction heating actuators 120 may therefore be used to control the caliper (thickness) profile of the paper sheet 108. The nips of a calender may also be equipped with other actuator arrays, such as arrays of air showers or steam showers, which may be used to control the gloss profile or smoothness profile of the paper sheet.

Two additional actuators 122-124 are shown in FIG. 1. A thick stock flow actuator 122 controls the consistency of the incoming stock received at the headbox 112. A steam flow actuator 124 controls the amount of heat transferred to the paper sheet 108 from drying cylinders. The actuators 122-124 could, for example, represent valves controlling the flow of stock and steam, respectively. These actuators may be used for controlling the dry weight and moisture of the paper sheet 108. Additional components could be used to further process the paper sheet 108, such as a supercalender (for improving the paper sheet's thickness, smoothness, and gloss) or one or more coating stations (each applying a layer of coatant to a surface of the paper to improve the smoothness and printability of the paper sheet). Similarly, additional flow actuators may be used to control the proportions of different types of pulp and filler material in the thick stock and to control the amounts of various additives (such as retention aid or dyes) that are mixed into the stock.

This represents a brief description of one type of paper machine 102 that may be used to produce a paper product. Additional details regarding this type of paper machine 102 are well-known in the art and are not needed for an understanding of this disclosure. Also, this represents one specific type of paper machine 102 that may be used in the system 100. Other machines or devices could be used that include any other or additional components for producing a paper product. In addition, this disclosure is not limited to use with systems for producing paper products and could be used with systems that process the produced paper or with systems that produce or process other items or materials, such as plastic, textiles, metal foil or sheets, or other or additional materials that are manufactured or processed as moving sheets.

In order to control the paper-making process, one or more properties of the paper sheet 108 may be continuously or repeatedly measured. The sheet properties can be measured at one or various stages in the manufacturing process. This information may then be used to adjust the paper machine 102, such as by adjusting various actuators within the paper machine 102. This may help to compensate for any variations of the sheet properties from desired targets, which may help to ensure the quality of the sheet 108.

As shown in FIG. 1, the paper machine 102 includes a scanner 126, which may include one or more sensors. The scanner 126 is capable of scanning the paper sheet 108 and measuring one or more characteristics of the paper sheet 108. For example, the scanner 126 could include sensors for measuring the color, gloss, sheen, haze, surface features (such as roughness, topography, or orientation distributions of surface features), or any other or additional characteristics of the paper sheet 108.

The scanner 126 includes any suitable structure or structures for measuring or detecting one or more characteristics of the paper sheet 108, such as sets or arrays of sensors. A scanning or moving set of sensors represents one particular embodiment for measuring sheet properties. Other embodiments could be used, such as those using stationary sets or arrays of sensors, deployed in one or a few locations across the sheet or deployed in a plurality of locations across the whole width of the sheet such that substantially the entire sheet width is measured.

The controller 104 receives measurement data from the scanner 126 and uses the data to control the paper machine 102. For example, the controller 104 may use the measurement data to adjust the various actuators in the paper machine 102 so that the paper sheet 108 has properties at or near desired properties. The controller 104 includes any hardware, software, firmware, or combination thereof for controlling the operation of at least part of the paper machine 102, such as a proportional-integral-derivative (PID) controller or a cross-direction machine-direction (CDMD) model predictive controller (MPC). In this example, the controller 104 includes at least one processor 128, at least one memory 130 storing instructions and data used, generated, or collected by the processors, and at least one network interface 132.

The network 106 is coupled to the controller 104 and various components of the paper machine 102 (such as the actuators and the scanner 126). The network 106 facilitates communication between components of system 100. The network 106 represents any suitable network or combination of networks facilitating communication between components in the system 100. The network 106 could, for example, represent a wired or wireless Ethernet network, an electrical signal network (such as a HART or FOUNDATION FIELDBUS network), a pneumatic control signal network, or any other or additional network(s).

As described in more detail below, during operation of the paper machine 102, the paper sheet 108 may have a variable location, tilt, or other geometry with respect to the scanner 126. As a result, measurements of a sheet property taken by the sensors in the scanner 126 are typically "biased," meaning the measurements are taken at an undesired or other geometry that is not the nominal or ideal geometry for the measurement. To compensate for this, multiple biased measurements from the sensors are used to determine an unbiased measurement of the sheet property. The "unbiased" measurement represents a measurement of the sheet property estimated to occur at the nominal or ideal geometry for the measurement.

In this way, the paper sheet 108 is allowed to move during measurements of one or more sheet properties. Rather than attempting to suppress geometric variation of the sheet 108, variations of the sheet 108 are used to assist in the measurement of the sheet's properties. In fact, additional geometric variations can be induced in the sheet 108 to ensure that an adequate number of biased measurements are obtained. This reduces or eliminates the need for sheet stabilization mechanisms near the sensors. Moreover, measurements of the sheet's properties can actually benefit from increased geometric variations, which can be easily implemented.

Although FIG. 1 illustrates an example paper production system 100, various changes may be made to FIG. 1. For example, other systems could be used to produce paper products or other products. Also, while shown as including a single paper machine 102 with various components and a single controller 104, the production system 100 could include any number of paper machines or other production machinery having any suitable structure, and the system 100 could include any number of controllers. In addition, FIG. 1 illustrates one operational environment in which biased measurements of an unstable sheet can be used to determine unbiased sheet properties. This functionality could be used in any other suitable system.

Figure 2:
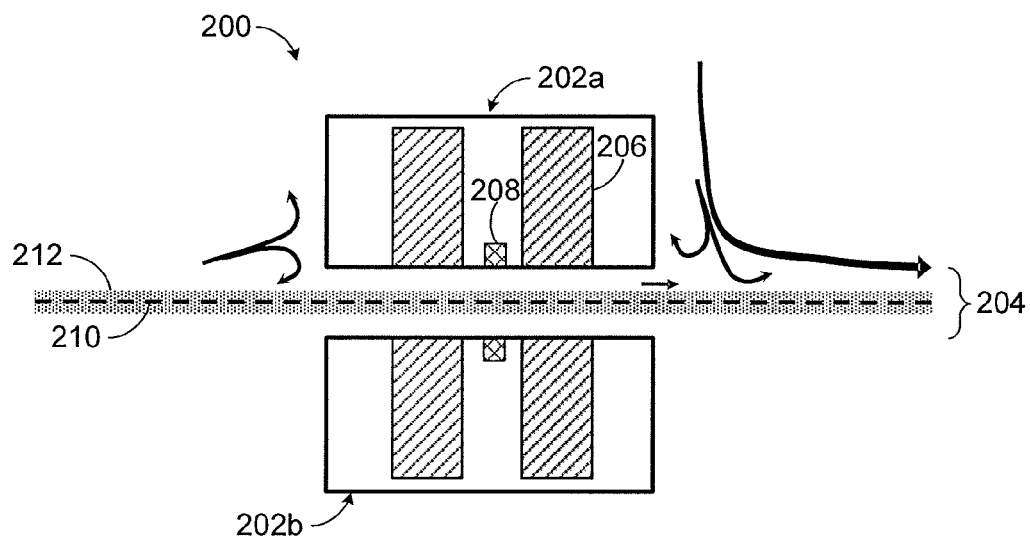
FIG. 2 illustrates an example sensor assembly for measuring properties of an unstabilized moving sheet according to this disclosure.

FIG. 2 illustrates an example sensor assembly 200 for measuring properties of an unstabilized moving sheet according to this disclosure. The sensor assembly 200 could represent one example implementation of the scanner 126. In this example, the sensor assembly 200 includes two sensor carriages 202a-202b separated by a gap 204 through which the sheet 108 travels. Each of the sensor carriages 202a-202b includes one or multiple sensors 206. The sensors 206 measure one or more characteristics of the sheet 108, such as color, gloss, sheen, haze, surface features, or any other or additional characteristics of the sheet 108. Each sensor 206 includes any suitable structure for measuring one or more characteristics of a sheet of material, such as a photosensor, ionization chamber, spectrograph, camera, or mechanical sensor. A mechanical sensor could include a contacting or non-contacting caliper probe. Each sensor 206 could have any suitable arrangement and position relative to the sheet 108.

Each of the sensor carriages 202a-202b also includes a mechanism for measuring the sheet's geometry at one or more locations. For example, one or more of the sensor carriages 202a-202b could include at least one geometry sensor 208, which can use any suitable technique to identify a distance, location, tilt, or other geometric feature(s) of the sheet 108 with respect to the sensors 206. One example technique that can be used by the sensor 208 is triangulation using a projected optical pattern and an image detector, which is described below.

In this example, the sheet 108 moves through the gap 204 between the sensor carriages 202a-202b. Ideally, the sheet 108 would travel along a nominal path 210 between the sensor carriages 202a-202b (with no tilt). In actuality, the sheet 108 typically moves within the gap 204. For example, turbulent overpressure where the sheet 108 enters the gap 204 and turbulent underpressure where the sheet 108 exits the gap 204 typically lead to instability in the sheet's geometry. Also, variations in the tension of the sheet 108 often lead to different sheet positions and angles. In addition, high shear and turbulence in the gap 204 can lead to varying positions and tilts of the sheet 108. As a result, the sheet 108 can have varying positions and tilts within the gap 204, which are typically within an envelope 212.

The varying geometries of the sheet 108 can result in biased measurements by the sensors 206. For example, variable geometries can introduce bias to many surface measurements. These biases can include bias due to variable deviations from nominal illumination intensity distributions or directionality on the sheet's surface. These biases can also include variable directional bias to shadows and feature contrast, as well as variable deviations from nominal direction for specular and specific aspecular reflections. Compensation for known geometric deviations is typically not feasible in most cases. Biases in measurements are often nonergodic, meaning filtering is not helpful. Also, adjustments of measurements from one geometry to another often require a model of sensitivity to geometric variation, which is typically not available beforehand. In addition, such a model often requires parameters for variation of the sheet property to be measured with changes in geometry. Existing solutions that attempt to stabilize a sheet for measurement purposes are often of limited success.

In accordance with this disclosure, the sheet 108 is not stabilized for measurement by the sensors 206, meaning variations in the geometry of the sheet 108 with respect to the sensors 206 are allowed. Instead, the geometry sensors 208 measure the geometry of the sheet 108, such as by measuring at least one pass plane angle of the sheet 108 or the distance to at least one point on the sheet 108. Using the sensors 206, biased measurements of a sheet property are made at each of multiple known geometries (which may or may not include the nominal geometry). An unbiased measurement of the sheet property can then be determined from the set of biased measurements and their measurement geometries. Other values could also be determined using the biased measurements, such as the sheet property's sensitivity to variations in geometry or a robustness estimate for the unbiased measurement. The same process or a similar process could be used repeatedly to measure one or multiple properties of the sheet 108.

Additional details regarding this technique for using biased measurements to determine unbiased measurements of a sheet property are shown in FIGS. 3 through 6, which are described below. Note that any suitable component(s) could be used to calculate unbiased measurements of sheet properties using biased measurements, such as the sensor assembly 200, the controller 104, or a stand-alone or other unit. Also note that this technique can be used with any suitable measurements of any suitable properties of a sheet. Example measurements can include scalar, one-dimensional, or two-dimensional optical measurement made using one or more independent wavelength bands or spectroscopic measurements. Example sheet properties can include statistical properties such as roughness or topography of the sheet's surface, geometric properties of embossed or impressed markings on the sheet's surface, or orientation distributions of piecewise linear surface features (like fibers or edges of markings) on the sheet's surface. Other example sheet properties can include measurements of quantities integrated over areas of the sheet's surface, such as color, gloss, sheen, or haze.

Although FIG. 2 illustrates an example sensor assembly 200 for measuring properties of an unstabilized moving sheet, various changes may be made to FIG. 2. For example, any number of sensor carriages 202a-202b could be used (including a single sensor carriage). Also, each sensor carriage could include any number of sensors 206 and/or geometry sensors 208 in any suitable arrangement. In addition, it may be noted that some stabilization could be used with the sheet 108, such as to ensure that the sheet 108 remains within a specified envelope 212 within the gap 204. However, the stabilization may allow for at least some movement of the sheet 108 within the gap 204 and the collection of biased measurements.

Figure 3:
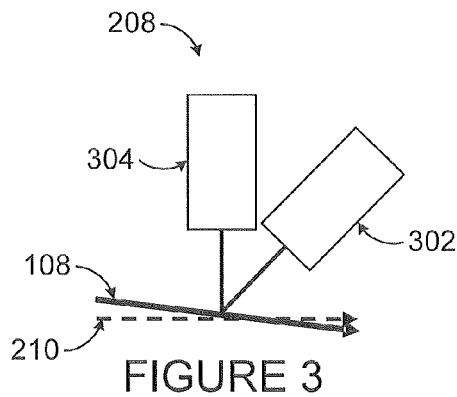
FIG. 3 illustrates an example geometry sensor for measuring a geometry of an unstabilized moving sheet according to this disclosure.

FIG. 3 illustrates an example geometry sensor 208 for measuring a geometry of an unstabilized moving sheet according to this disclosure. In this example, the geometry sensor 208 includes a projector 302 and a detector 304. The projector 302 projects an image onto the sheet 108, such as an image of one or more spots, lines, or patterns (like a grid). The projector 302 includes any suitable structure for projecting at least one image onto a sheet 108. The detector 304 captures the image from the projector 302 that has reflected off the sheet 108. The detector 304 represents any suitable image-capturing device, such as a charge-coupled device (CCD), a complimentary metal oxide semiconductor (CMOS) device, or a charge injection device (CID).

As noted above, the sheet 108 may have an unstable geometry when being measured by the sensors 206. That variation in geometry is used to obtain multiple biased measurements of a sheet property. Natural variation in the geometry of the sheet 108 (such as variations in time and geometric parameter ranges) is often sufficient to obtain an adequate range of biased measurements. The adequacy of the variations can be assessed from the measurements of the sheet geometry performed by the geometry sensor 208. In this example, the geometry sensor 208 measures the geometry of the sheet 108 with respect to one or more sensors 206, such as by measuring at least one pass plane angle of the sheet 108 or the distance of the sheet 108 from one or more points.

Figure 4A:
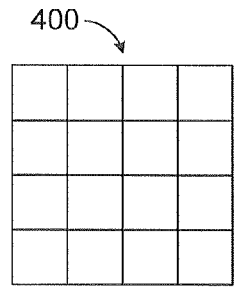
FIGS. 4A and 4B illustrate an example technique for determining a geometry of an unstabilized moving sheet according to this disclosure.
Figure 4B:
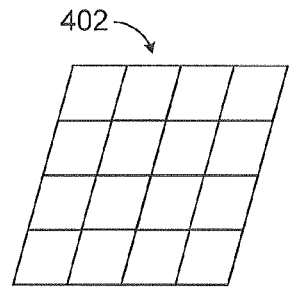

Any suitable technique can be used to measure the geometry of the sheet 108 using one or more geometry sensors 208. One technique includes projecting a known grid or other optical pattern onto the sheet 108 using the projector 302 and measuring the projected shape on the sheet 108 using the detector 304. The geometry of the sheet 108 can be estimated based on the difference between the actual image of the projected pattern and the nominal or ideal image of the projected pattern (the pattern when projected onto a sheet 108 in its nominal position). An example of this is shown in FIGS. 4A and 4B, where pattern 400 could represent the nominal or ideal image of a projected grid and pattern 402 could represent the actual image of the projected grid. Based on the distortion axis and aspect ratio of the actual image, for instance, it is possible to determine the angle or orientation of the sheet 108 with respect to the geometry sensor 208. Also, based on the central intersection of the projected grid, for instance, it is possible to measure the distance of the sheet 108 from the geometry sensor 208. Other techniques could also be used, such as multi-point triangulation using lasers or other distance measuring devices.

Note that the geometry measurements performed by the geometry sensor 208 can be done so as to not interfere with measurements performed by the sensors 206. For example, the geometry measurements can employ light in one or more wavelength ranges that do not overlap with one or more wavelength ranges used by the sensors 206. Also, one or more compensation techniques could be used to prevent geometry measurement light from interfering with measurements taken by the sensors 206. For instance, the geometry measurements can employ light in one or more narrow wavelength bands that are within the wavelength range(s) used by the sensors 206. One or more narrowband filters could then be used to exclude the wavelengths used by the geometry sensor 208 from being received and used by the sensors 206. Additionally or alternatively, a geometry measurement performed by the geometry sensor 208 and a measurement performed by the sensors 206 may be sequential in time, where the measurements are taken in a time interval short enough that the geometry has not changed significantly. In addition, by measuring the geometry before and after the measurement by the sensors 206, an average geometry can be inferred for the measurement by the sensors 206.

Although FIG. 3 illustrates an example geometry sensor 208 for measuring a geometry of an unstabilized moving sheet, various changes may be made to FIG. 3. For example, the placement and orientation of the components in FIG. 3 are for illustration only. Also, any other suitable technique could be used to determine the geometry of the sheet 108. Although FIGS. 4A and 4B illustrate an example technique for determining a tilt angle of a sheet 108, various changes may be made to FIGS. 4A and 4B. For example, any suitable image could be projected onto the sheet 108.

Figure 5A:
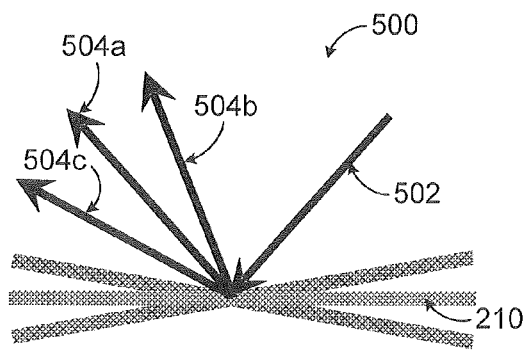
FIGS. 5A and 5B illustrate example measurements of an unstabilized sheet according to this disclosure.
Figure 5B:
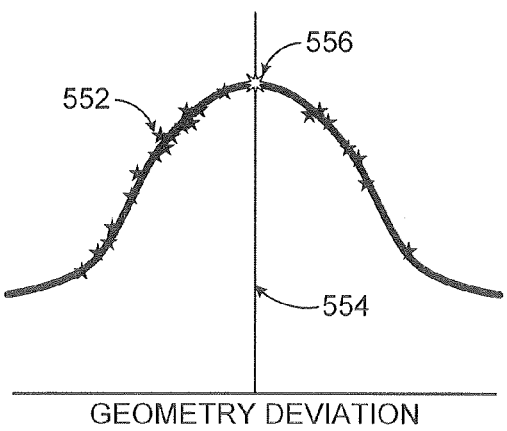

FIGS. 5A and 5B illustrate example measurements of an unstabilized sheet according to this disclosure. As shown in FIG. 5A, an incident ray 502 can be reflected off the sheet 108. Ideally, the sheet 108 is in the nominal position 210, producing a resulting ray 504a having a nominal direction. A measurement of the ray 504a may therefore produce an unbiased measurement of a property of the sheet 108. However, movement of the sheet 108 may actually produce another ray, such as 504b or 504c, that has a different direction. A measurement of the ray 504b or 504c may therefore produce a biased measurement of the sheet property.

Multiple biased measurements of the sheet property can be used to estimate an unbiased measurement of the sheet property. Each biased measurement is taken at a known geometry of the sheet 108 (as determined by the geometry sensors 208), meaning the sheet's geometry can be measured substantially simultaneously with each measurement taken by the sensors 206. The measurements taken by the sensors 206 could have a measurement interval that is short enough so that the sheet's geometry does not change significantly during a single measurement interval. This allows the geometry of the sheet 108 to be known for each of the measurements taken by the sensors 206.

The sensor measurements that are ultimately associated with the known geometries could include raw measurements (such as light intensities or image contrasts) or intermediate quantities (such as estimated scattering coefficients or image Fourier spectra). The sensor measurements associated with the known geometries could also include biased surface properties (such as gloss or roughness) estimated from raw measurements without compensation for geometric perturbations.

A set of measurements by the sensors 206 (and their corresponding geometries) are determined over one or more measurement intervals. The measurements by the sensors 206 could be initiated based on the geometry measurements taken by the geometry sensors 208 or in response to any other suitable trigger(s). The measurements by the sensors 206 may or may not be spaced apart equally in time.

An example set of measurements is shown in FIG. 5B, where points 552 denote multiple biased measurements of a sheet property. Each of those points 552 is plotted against the deviation of the sheet's geometry with respect to a nominal geometry 554 for that measurement. The set of measurements can span an adequate range of geometries, such as by including measurements on both sides of the nominal geometry 554 or by obtaining measurements suitably close to the nominal geometry 554.

An unbiased measurement of the sheet property can be estimated from this set of measurements (and their known measurement geometries). The unbiased measurement is denoted by point 556 in FIG. 5B, where the unbiased measurement occurs at the nominal geometry 554. Any suitable technique could be used to estimate the unbiased measurement based on the set of biased measurements, such as parametric or nonparametric regression or interpolation. Example nonparametric regression techniques could include kernel smoothing, Savitzky-Golay filtering, wavelet filtering, variance partitioning, or factor analysis (including functional-data variants). Example parametric regression techniques could include using one or more known function forms (including empirical, theoretical, or arbitrary forms). Again, note that the selected estimation technique may operate using raw or intermediate measurements of the sheet's property. Also note that if an actual measurement of the sheet property occurs at the sheet's nominal geometry 554, the estimation of an unbiased measurement may or may not be performed.

While FIG. 5B depicts only a single axis for geometry deviation, in practice there can be more than one degree of freedom for the geometry. For example, there may be variations in a working distance from a sensor 206 to a sheet 108. There may also be variations in one or more angles describing the tilt of the sheet 108. There may further be variations in one or more radii describing curvature of the sheet 108. The measured geometry deviation may thus involve more than one axis, and the estimation technique may incorporate compensation for more than one axis of geometric deviation. Each axis of geometric deviation in the estimation may be the measured geometric parameter or a transformation of the measured geometric parameter value. For instance, instead of a radius of curvature, the inverse of a radius of curvature may be used. Similarly, instead of a tilt angle, the cosine of a tilt angle may be used.

The estimation process produces an unbiased measurement of the sheet's property at a nominal geometry. Optionally, the estimation process can produce a parametric sensitivity or other sensitivity value of the sheet property to geometric variations (such as value intervals or partial derivatives of the estimated sheet property). The estimation process can also optionally produce an estimate of measurement robustness, such as a range of sheet property values estimated using subsets of the biased measurement set. The subset of measurement values could be obtained in any suitable manner, such as by generating random-size subsets or subsets where a number of random samples are omitted.

Note that the set of biased measurements may include measurements associated with any suitable geometric variations, such as geometric variations on both sides of the nominal geometry 554. Various techniques could also be used to enhance the geometric variations of the measurements. These can include techniques to enhance the sheet's geometric variations during a measurement time-frame, to extend or attenuate the range of geometric variations, or to adjust the rapidity of variation so that sufficient measurements exist. Any suitable deterministic or random disturbances of the sheet's path can be used to vary the geometry of the sheet 108. This may include air pulses or air flows of varying strengths, durations, or directions. Other techniques could include one or more moving aerodynamic elements (such as tilting airfoils) with varying angles for varying durations. In addition, rather than varying the sheet 108, variations could be made to the sensor assembly 200 itself, such as by using one or more moving sensor elements (such as moving illuminators, detectors, mirrors, or lenses).

The distribution of biased measurements at different geometries (together with the knowledge of the geometry at which each measurement was made) allows for the evaluation of one or more sheet properties at a nominal geometry, as well as a determination of the sensitivity of the measurements to geometric perturbations. This may therefore represent a superior measurement technique that is a superset of traditional measurement results. This technique does not require that any measurements occur at the nominal geometry during any measurement instant.

Although FIGS. 5A and 5B illustrate example measurements of an unstabilized sheet 108, various changes may be made to FIGS. 5A and 5B. For example, any number of measurements having any suitable distribution could be obtained. Also, the bell-shaped pattern of the biased and unbiased measurements shown in FIG. 5B is for illustration only. Biased and unbiased measurements of a sheet property could have any other suitable pattern. In addition, this technique could be used with one or multiple sheet properties, and different sheet properties could have different biased measurements and nominal geometries.

Figure 6:
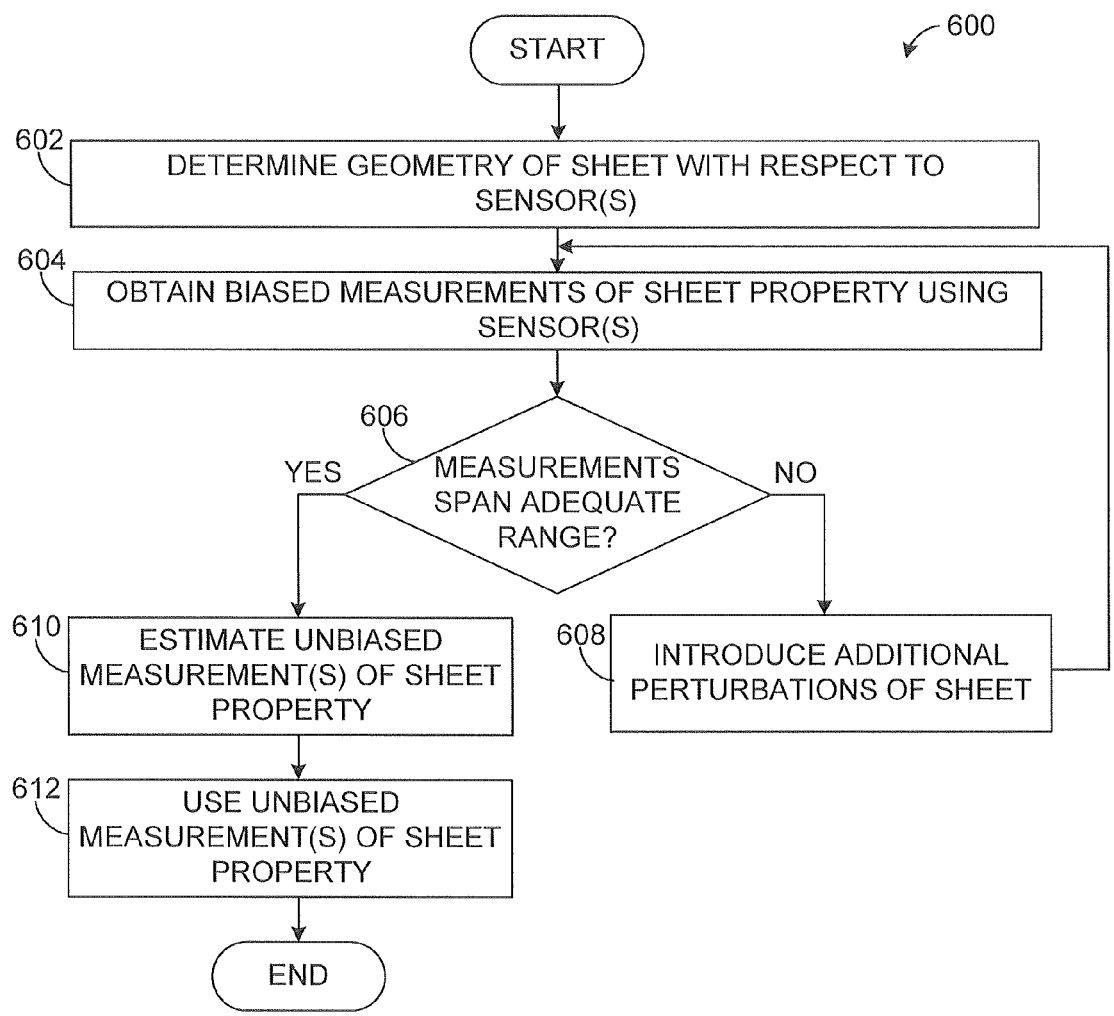
FIG. 6 illustrates an example method for measuring properties of an unstabilized moving sheet according to this disclosure.

FIG. 6 illustrates an example method 600 for measuring properties of an unstabilized moving sheet according to this disclosure. A geometry of a sheet with respect to one or more sensors is determined at step 602. This could include, for example, using the geometry sensors 208 to determine the tilt angle or position of the sheet 108. Measurements of one or more sheet properties are obtained at step 604. This could include, for example, using the sensors 206 to measure one or more properties of the sheet 108. Since the geometry of the sheet 108 is likely not nominal here, most or all of these measurements represent biased measurements.

A determination is made whether the biased measurements span an adequate range of geometries at step 606. This could include, for example, determining if the biased measurements span an adequate range of geometries or if an adequate number of biased measurements are within a specified range around the nominal geometry. If not, additional perturbations are introduced in the sheet at step 608. This could include, for example, causing additional movements of the sheet 108 using varying air flows or airfoils or by adjusting the sensor assembly 200.

Otherwise, one or more unbiased measurements are estimated for the one or more sheet properties at step 610. This could include, for example, using the biased measurements of a sheet property to estimate an unbiased measurement of the sheet property at a nominal geometry. This could be done using regression or other suitable technique. The one or more unbiased measurements are used in any suitable manner at step 612. This could include, for example, using the one or more unbiased measurements to adjust operation of the system producing the sheet being measured. This could also include storing the one or more unbiased measurements for historical analysis or other later use, transmitting the one or more unbiased measurements to any suitable destination(s), or otherwise using the one or more unbiased measurements.

Although FIG. 6 illustrates an example method 600 for measuring properties of an unstabilized moving sheet, various changes may be made to FIG. 6. For example, while shown as a series of steps, various steps in FIG. 6 may overlap, occur in parallel, occur in a different order, or occur multiple times.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
    receiving multiple biased measurements associated with a surface property of a sheet of material, the biased measurements (i) taken in real-time at different times while the sheet of material moves in a manufacturing process and (ii) corresponding to different known sheet geometries of the sheet of material caused by variable movement of the sheet of material during the manufacturing process;
    determining, using one or more processing devices, an unbiased measurement of the surface property of the sheet of material using a regression or interpolation technique with the multiple biased measurements taken at the different times and corresponding to the different known geometries of the sheet of material, the unbiased measurement corresponding to a value of the surface property of the sheet estimated to occur at a nominal sheet geometry selected for measuring the surface property of the sheet of material; and
    causing a system producing the sheet of material using the manufacturing process to adjust production of the sheet of material based on the unbiased measurement;
    wherein the surface property of the sheet of material comprises at least one of: a color, a gloss, a sheen, a haze, a surface feature, a roughness, a surface topography, or a distribution of surface features of the sheet.

2. The method of claim 1, wherein determining the unbiased measurement using the regression or interpolation technique comprises performing regression using the biased measurements and their corresponding sheet geometries to identify the value of the surface property of the sheet estimated to occur at the nominal sheet geometry.

3. The method of claim 1, wherein at least some of the multiple biased measurements of the surface property of the sheet are different based on variations associated with the multiple sheet geometries.

4. The method of claim 3, wherein the multiple sheet geometries comprise at least one of: different tilt angles of the sheet, different curvatures of the sheet, and different distances of the sheet from at least one sensor.

5. The method of claim 1, further comprising measuring the multiple sheet geometries of the sheet by projecting a known image onto the sheet and capturing the image reflected off the sheet.

6. The method of claim 1, wherein the system comprises a paper production system and the sheet comprises a paper sheet.

7. The method of claim 6, wherein adjusting the production of the sheet of material comprises adjusting one or more actuators in the paper production system.

8. The method of claim 1, further comprising:
    generating the biased measurements using one or more sensors.

9. The method of claim 8, wherein the sheet is not stabilized during the generation of the biased measurements.

10. The method of claim 1, further comprising:
    when the multiple biased measurements do not span an adequate range, generating disturbances in a path of the sheet of material to create additional sheet geometries that vary at least one of a tilt angle, a curvature, and a position of the sheet;
    wherein:
        determining the unbiased measurement using the regression or interpolation technique comprises performing parametric regression using the biased measurements and their corresponding sheet geometries to identify the value of the surface property of the sheet estimated to occur at the nominal sheet geometry;
        each of the multiple sheet geometries is determined by projecting a known image onto the sheet, capturing the image reflected off the sheet, and using a distortion axis and an aspect ratio of the captured image to determine the sheet geometry;
        each biased measurement is measured at a same time as its corresponding sheet geometry time, wherein a sensor used to obtain the biased measurement operates in a different wavelength band than a sensor used to measure the corresponding sheet geometry; and
        the one or more processing devices comprise a cross-direction machine-direction (CDMD) model predictive controller configured to receive the multiple biased measurements and determine the unbiased measurement of the surface property.

11. An apparatus comprising:
    at least one memory configured to store multiple biased measurements associated with a surface property of a sheet of material, the biased measurements (i) taken in real-time at different times while the sheet of material moves in a manufacturing process and (ii) corresponding to different known sheet geometries of the sheet of material caused by variable movement of the sheet of material during the manufacturing process; and
    at least one processor configured to:
        determine an unbiased measurement of the surface property of the sheet of material using a regression or interpolation technique with the multiple biased measurements taken at the different times and corresponding to the different known geometries of the sheet of material, the unbiased measurement corresponding to a value of the surface property of the sheet estimated to occur at a nominal sheet geometry selected for measuring the surface property of the sheet of material; and cause a system producing the sheet of material using the manufacturing process to adjust production of the sheet of material based on the unbiased measurement;

wherein the surface property of the sheet of material comprises at least one of: a color, a gloss, a sheen, a haze, a surface feature, a roughness, a surface topography, or a distribution of surface features of the sheet.

12. The apparatus of claim 11, wherein the at least one processor is configured to determine the unbiased measurement using the regression or interpolation technique by performing regression using the biased measurements and their corresponding sheet geometries to identify the value of the surface property of the sheet estimated to occur at the nominal sheet geometry.

13. The apparatus of claim 11, wherein the at least one processor is further configured to:
    determine whether the multiple sheet geometries associated with the biased measurements are adequate; and
    when the multiple sheet geometries associated with the biased measurements are not adequate, cause another device to generate disturbances in a path of the sheet of material to create additional sheet geometries that vary at least one of a tilt angle, a curvature, and a position of the sheet.

14. The apparatus of claim 11, wherein the at least one processor is further configured to measure the multiple sheet geometries of the sheet.

15. The apparatus of claim 14, wherein the at least one processor is configured to measure the multiple sheet geometries of the sheet by analyzing a known image projected onto and reflected off the sheet.

16. The apparatus of claim 11, wherein:
    the system comprises a paper production system configured to produce a paper sheet; and
    the at least one processor is configured to adjust the operation of the system by adjusting one or more actuators in the paper production system.

17. A non-transitory computer readable storage medium embodying a computer program, the computer program comprising:
    computer readable program code for obtaining multiple biased measurements associated with a surface property of a sheet of material, the biased measurements (i) taken in real-time at different times while the sheet of material moves in a manufacturing process and (ii) corresponding to different known sheet geometries of the sheet of material caused by variable movement of the sheet of material during the manufacturing process;
    computer readable program code for determining an unbiased measurement of the surface property of the sheet of material using a regression or interpolation technique with the multiple biased measurements taken at the different times and corresponding to the different known geometries of the sheet of material, the unbiased measurement corresponding to a value of the surface property of the sheet estimated to occur at a nominal sheet geometry selected for measuring the surface property of the sheet of material; and
    computer readable program code for adjusting operation of a system producing the sheet of material based on the unbiased measurement;
    wherein the surface property of the sheet of material comprises at least one of: a color, a gloss, a sheen, a haze, a surface feature, a roughness, a surface topography, or a distribution of surface features of the sheet.

18. The computer readable storage medium of claim 17, wherein the computer readable program code for determining the unbiased measurement comprises computer readable program code for performing regression using the biased measurements and their corresponding sheet geometries to identify the value of the surface property of the sheet estimated to occur at the nominal sheet geometry.

19. The computer readable storage medium of claim 17, further comprising:
    computer readable program code for measuring the multiple sheet geometries of the sheet.

20. The computer readable storage medium of claim 17, further comprising:
    computer readable program code for determining whether the multiple sheet geometries associated with the biased measurements are adequate; and
    computer readable program code, responsive to a determination that the multiple sheet geometries associated with the biased measurements are not adequate, for causing another device to generate disturbances in a path of the sheet of material for creating additional sheet geometries that vary at least one of a tilt angle, a curvature, and a position of the sheet.

* * * * *